United States Patent
Borredon et al.

(10) Patent No.: US 6,794,547 B2
(45) Date of Patent: Sep. 21, 2004

(54) PROCESS FOR THE SYNTHESIS OF ARYL ALKYL MONOETHERS

(75) Inventors: Elisabeth Borredon, Tournefeuille (FR); Antoine Gaset, Toulouse (FR); Samedy Ouk, Toulouse (FR); Sophie Thiebaud-Roux, L'Union (FR); Pierre Le Gars, Toulouse (FR)

(73) Assignee: SNPE, Paris Cedex (FR)

( * ) Notice: Subject to any disclaimer, the term of this patent is extended or adjusted under 35 U.S.C. 154(b) by 0 days.

(21) Appl. No.: 10/079,460

(22) Filed: Feb. 20, 2002

(65) Prior Publication Data

US 2002/0193641 A1 Dec. 19, 2002

(30) Foreign Application Priority Data

Feb. 23, 2001 (FR) .............................. 01 02493

(51) Int. Cl.⁷ .............................. C07C 41/00
(52) U.S. Cl. ...................... 568/628; 568/650
(58) Field of Search ................ 568/628, 650; 560/64, 67

(56) References Cited

U.S. PATENT DOCUMENTS

| 4,192,949 A | 3/1980 | Merger et al. ................. 560/67 |
| 4,254,276 A | 3/1981 | Iori et al. ..................... 560/64 |

FOREIGN PATENT DOCUMENTS

| EP | 104598 | 11/1984 |
| FR | 2595959 | 9/1987 |
| JP | 62246533 | 10/1987 |
| JP | 6145091 | 5/1994 |

OTHER PUBLICATIONS

Lee et al, Convenient O–Methylation of Phenols with Dimethyl Carbonate, Synlett, pp. 1063–1064, Oct. 1998.
Bomben et al, A Continuous Flow O–Methylation of Phenols with Dimethyl Carbonate, etc., Ind. Eng. Chem. Res., vol. 38,pp. 2075–2079, 1999.
Ono, Dimethyl Carbonate For Environmentally Benign Reactions, Pure Appl. Chem., vol. 68, No. 2, pp. 367–375, 1996—Abstract.
Lee et al, O–Alkylation of Phenol Derivatives Over Basic Zeolites, Catal. Today, vol. 44(1–4) pp. 253–258, 1998.
Lissel et al, Use of Dimethyl Carbonate as a Methylating Agent, etc., Synthesis, vol. 5, pp. 382–383, 1986(German language with Chemical Abstracts in English.
Tundo et al, Continuous Flow Processes Under Gas–Liquid, etc., Ind. Eng. Chem. Res., vol. 27, pp. 1565–1571, 1988.

*Primary Examiner*—Johann Richter
*Assistant Examiner*—Sikarl A. Witherspoon
(74) *Attorney, Agent, or Firm*—Bucknam and Archer

(57) ABSTRACT

The invention relates to a process for the synthesis of aryl alkyl monoethers by reaction of a phenol compound, comprising one or more hydroxyl groups attached to the aromatic system, and of a dialkyl carbonate. It is a solvent-free process carried out at a pressure of between $0.93 \times 10^5$ Pa and $1.07 \times 10^5$ Pa, at a temperature of between 100° C. and 200° C., and in the presence of a catalyst chosen from the group consisting of alkaline carbonates and alkaline hydroxides. The dialkyl carbonate is added gradually to the reaction mixture.

10 Claims, No Drawings

PROCESS FOR THE SYNTHESIS OF ARYL ALKYL MONOETHERS

The present invention relates to a process for the synthesis of aryl alkyl ethers.

It relates more particularly to a process for the improved synthesis of aryl alkyl ethers by O-alkylation of the corresponding phenol compounds.

Aryl alkyl ethers are very useful intermediates, in particular for the preparation of dyes, plant-protection agents and fragrances. Their applications are reported in particular in Ullmann Enzyklopädie der Technischen Chemie, Volume 13, pages 450–453 and Volume 14, pages 760–763. A great many preparation processes have consequently been provided.

Some consist in alkylating phenol derivatives with alkyl halides or alkyl sulphates, as indicated in Pure & Applied Chemistry, Volume 68, No. 2, pages 367–375 (1996). However, these processes exhibit numerous disadvantages. Some reactants, such as dimethyl sulphate, are highly toxic. Furthermore, the acid released during the reaction must be neutralized; in point of fact, some phenols are highly sensitive to the neutralizing agents.

Other processes use an alcohol, for example methanol, as alkylating agent. The reaction is carried out at very high temperatures of greater then 250° C. In the majority of cases, this reaction is not selective and C-alkylation by-products are formed. When it is selective, the degree of conversion is low. Such a process is described in Volume 44 of Catalysis Today, pages 253–258 (1998).

Processes for alkylation by dialkyl carbonates were then envisaged, in particular processes for O-alkylation by dimethyl carbonate. The catalyst used is chosen from tertiary amine salts, diamines, quaternary ammonium salts or tertiary phosphines. Such processes are disclosed, for example, in U.S. Pat. No. 4,192,949. However, the reaction temperature, pressure and duration of these syntheses, carried out in a closed reactor, remain high, which is highly disadvantageous industrially.

In order to prepare aryl alkyl esters under milder conditions, the authors of the article which appeared in Synthesis, Volume 5, pages 382–383 (1986), recommend the use of potassium carbonate with a cocatalyst, crown ether 18–6. This is catalysis by solid/liquid phase transfer. The reaction is carried out at atmospheric pressure and at 100° C. but the high toxicity and the high cost of the phase transfer cocatalyst, the crown ether, are major disadvantages. Furthermore, the mean rate of formation of ether per mole of catalyst is of the order of 0.03 mol per hour, which is low. Another catalytic system was then proposed, in order to operate with nontoxic reactants. This is still phase transfer catalysis. Such a process is described in Industrial & Engineering Chemistry Research, volume 27, pages 1565–1571 (1988). Tundo et al. use, as catalytic system, polyethylene glycol adsorbed on a solid stationary bed composed either of potassium carbonate or of α-alumina beads. In the latter case, potassium carbonate is also adsorbed on the α-alumina beads. This process exhibits the disadvantage of using a complex catalytic system with at least two constituents, polyethylene glycol and potassium carbonate. The simultaneous presence of these two constituents is essential in obtaining a good yield. This is because, by way of comparison, when the catalytic system is composed of α-alumina beads covered solely with 5% by weight of potassium carbonate, the conversion of phenol to anisole, as indicated in FIG. 4, is 25%, which is very low. Furthermore, the heterogeneity of the reaction mixture reduces the efficiency of the reaction. The mean rate of formation of the ether per mole of catalyst is consequently only 0.13 mol per hour.

A similar continuous process was envisaged by Bomben et al. in an article which appeared in Industrial & Engineering Chemistry Research, Volume 38, pages 2075–2079 (1999). The authors of this article use, as catalytic system, a stirred catalytic bed composed of polyethylene glycol and of potassium carbonate. The disadvantages related to such a process remain still the complexity of the two-component catalytic system and the low value of the mean rate of formation of ether per mole of catalyst, which is only 0.7 mol/mol.h.

Another process, disclosed in Japanese Application JP 06145091, consists in reacting a phenol compound, such as phenol or hydroquinone, and an alkyl carbonate. The catalyst used is an alkali metal salt, in particular potassium carbonate. The reaction necessarily takes place in the presence of a nitrogenous organic solvent, such as pyridine, a formamide or an alkylacetamide. The authors have shown, in Comparative Example 1, that the yield was zero when the reaction was carried out without solvent. Furthermore, the reaction time remains long and the yields are low.

A person skilled in the art is therefore still looking for a process for the synthesis of aryl alkyl ethers which is inexpensive and selective, with a good yield, and for which the reaction conditions are mild, in particular as regards the pressure and the temperature.

Such a process is a subject-matter of the present invention.

The invention relates to a process for the synthesis of aryl alkyl monoethers by reaction of a phenol compound, comprising one or more hydroxyl groups attached to the aromatic cyclic system, and of a dialkyl carbonate, characterized in that the said process is carried out without solvent, at a pressure of between $0.93 \times 10^5$ Pa and $1.07 \times 10^5$ Pa, at a temperature of between 100° C. and 200° C., in the presence of a catalyst chosen from the group consisting of alkaline carbonates and alkaline hydroxides and in that the dialkyl carbonate is added gradually to the reaction mixture.

This process exhibits the advantage of being simple and inexpensive and makes it possible to obtain ethers with a very good yield.

This is because it is a solvent-free process using only a single catalyst. The use of a limited number of constituents thus reduces the cost. Furthermore, the operating conditions, in particular as regards the pressure and the temperature, are easy to implement industrially.

The reaction is selective. This is because, when the phenol compound comprises only one hydroxyl group on the aromatic cyclic system, only the corresponding aryl alkyl ether is obtained, without formation of by-products.

When the phenol compound comprises two or more hydroxyl groups attached to the aromatic cyclic system, an aryl alkyl monoether is predominantly obtained. Only small amounts of polyethers are obtained.

Another advantage of this process is the high value of the mean rate of formation of the ether with respect to the amount of catalyst used, which is of the order of 2 to 6 mol of ether formed per hour and per mole of catalyst used. With the already existing processes, the mean rate was less than or equal to 1 mol of ether formed per hour and per mole of catalyst.

This process makes it possible to selectively obtain a wide range of aryl alkyl monoethers starting from a dialkyl carbonate and a phenol compound.

The phenol compound is preferably chosen from the compounds of formula (I)

$$\underset{R^5}{\overset{R^3}{\underset{\displaystyle}{\bigodot}}}\overset{R^2}{\underset{R^6}{-OH}}\quad (I)$$

in which $R^2$, $R^3$, $R^4$, $R^5$ and $R^6$, which are identical or different, each represent a hydrogen atom,
a substituted or unsubstituted, saturated or unsaturated, $C_1$ to $C_{20}$ alkyl radical,
a substituted or unsubstituted aryl or aralkyl group,
a halogen atom,
a nitrile or nitro group or a group of formula:

$$R^7-\underset{O}{\overset{\|}{C}}-O-,\quad R^7-\underset{O}{\overset{\|}{C}}-S-,\quad R^7-\underset{O}{\overset{\|}{C}}-,$$

$$R^7-O-,\quad R^8-O-\underset{O}{\overset{\|}{C}}-,\quad R^8-S-,$$

$$R^9-\underset{O}{\overset{\|}{C}}-,\quad R^9-O\quad \text{or}\quad R^9-O-\underset{O}{\overset{\|}{C}}-,$$

in which $R^7$ is a $C_1$ to $C_{20}$ aliphatic radical, a $C_7$ to $C_{12}$ aralkyl radical or a $C_6$ to $C_{14}$ aromatic radical, $R^8$ is a $C_1$ to $C_{20}$ aliphatic radical, a $C_7$ to $C_{12}$ aralkyl radical or a $C_6$ to $C_{14}$ aromatic radical, and $R^9$ is a hydrogen atom, it being possible for two adjacent radicals, for example $R^2R^3$ or $R^3R^4$ or $R^4R^5$ or $R^5R^6$, to be connected to one another to form a saturated or unsaturated aliphatic ring, an aromatic ring or a saturated or unsaturated heterocycle which are unsubstituted or substituted by the groups as described for $R^2$ to $R^6$. The substituents of the $R^2$ to $R^6$ radicals are chosen in particular from halogen atoms, nitrile or nitro groups, or groups of formula:

$$R^7-\underset{O}{\overset{\|}{C}}-O-,\quad R^7-\underset{O}{\overset{\|}{C}}-S-,\quad R^7-\underset{O}{\overset{\|}{C}}-,$$

$$R^7-O-,\quad R^8-O-\underset{O}{\overset{\|}{C}}-,\quad R^8-S-,$$

$$R^9-\underset{O}{\overset{\|}{C}}-,\quad R^9-O\quad \text{or}\quad R^9-O-\underset{O}{\overset{\|}{C}}-,$$

in which $R^7$, $R^8$ and $R^9$ have the preceding meanings.

The compounds of formula I are known compounds which are commercially available or which are prepared according to known methods.

The preferred phenol compounds are phenol, p-cresol, 4-chlorophenol, 2-naphthol, 4-hydroxybenzophenone, 2,4-dihydroxybenzophenone and catechol.

The dialkyl carbonate is a carbonate for which the alkyl groups, which are preferably identical, are $C_1$ to $C_4$ groups. Preferably, the dialkyl carbonate is chosen from the group consisting of dimethyl carbonate and diethyl carbonate and better still the dialkyl carbonate used is dimethyl carbonate.

The amount of dialkyl carbonate used is generally between 0.9 and 5 mol and preferably from 1 to 2 mol with respect to the phenol compound.

The catalyst used is chosen from the group consisting of alkaline carbonates and alkaline hydroxides. The alkaline carbonates comprise both neutral alkaline carbonates and alkaline hydrogencarbonates.

Preferably, the alkaline ion is potassium and better still the catalyst used is neutral potassium carbonate.

The amount of catalyst used is between 0.01 and 0.1 mol per mole of phenol compound and preferably between 0.015 and 0.05 mol.

The reaction is carried out at a pressure of between $0.93 \times 10^5$ Pa and $1.07 \times 10^5$ Pa, i.e. at a pressure of between 700 mmHg and 800 mmHg. The local atmospheric pressure is generally within this range and the reaction is carried out at this pressure. The temperature is between 100° C. and 200° C. and preferably between 140° C. and 180° C.

It is a solvent-free process, that is to say a process without the introduction of a product other than the compounds of the reaction.

An implementation of the invention is now given.

The phenol compound, either completely or in part, the catalyst and optionally the final product, the already alkylated phenol compound, are placed initially in the reactor. The mixture is heterogeneous at ambient temperature. It is heated to a temperature of between 100° C. and 200° C., preferably of between 140° C. and 180° C. The mixture becomes homogeneous at the reaction temperature.

The dialkyl carbonate is then gradually introduced into the reaction mixture. Preferably, a small portion of the dialkyl carbonate is introduced into the mixture and then the dialkyl carbonate is introduced continuously with a flow rate of between 1 and 20 mol/h per mole of catalyst or by noncontinuous additions very close together in time.

When only a portion of the amount of phenol compound is present initially in the reactor, the other portion is added gradually to the reaction mixture, preferably simultaneous with the addition of dialkyl carbonate. Its flow rate is then preferably between 0.5 mol/h and 20 mol/h per mole of catalyst.

The alcohol produced during the reaction is distilled off as it is formed. The ether obtained can subsequently be purified by distillation.

This process is particularly well suited to the synthesis of aryl methyl monoethers, obtained by O-methylation of the corresponding phenol compound, by reaction of dimethyl carbonate with the phenol compound.

Very high yields, of greater than 95%, can be obtained by O-methylation, in particular starting from p-cresol, 4-chlorophenol and 2-naphthol.

Good yields are also obtained starting from phenol, 4-hydroxybenzophenone and 2,4-dihydroxybenzophenone.

This process is also particularly well suited to the synthesis of aryl ethyl monoethers, obtained by O-ethylation of the corresponding phenol compound, by reaction of diethyl carbonate with the phenol compound. Good yields are obtained, in particular starting from p-cresol.

The following examples illustrate, without implied limitation, alternative embodiments of the invention.

EXAMPLE 1

Synthesis of 4-methylanisole

The reaction is carried out in a 500 ml reactor. This reactor is surmounted by a cooling system at 20° C. The reactor is equipped with a thermometer, a mechanical stirrer and a feed system, such that it can be fed continuously throughout the reaction. 130 g of p-cresol, i.e. 1 200 mol, and 5.5 g of potassium carbonate, i.e. 40 mmol, i.e. 3.3 mol % with respect to the p-cresol, are introduced into the reactor.

The mixture is heated to 160° C. and this temperature is maintained throughout the synthesis.

16.2 g of dimethyl carbonate, i.e. 180 mmol, are then introduced. The reactor is subsequently fed continuously with dimethyl carbonate until the p-cresol has been completely consumed. Thus, over 7.5 hours, the reactor is fed with a continuous flow of 210 mmol/h of dimethyl carbonate.

The methanol produced is distilled off as it is formed. Subsequently, after purification by distillation, 142.2 g of 4-methylanisole, i.e. 1 164 mmol, are obtained, which corresponds to a yield of 97%.

The mean rate of formation of the 4-methylanisole for the amount of catalyst used is 3.9 mol/mol.h.

EXAMPLE 2

Synthesis of 4-methylanisole with Continuous Introduction of p-cresol

The assembly used is the same as that in Example 1. 21 g of p-cresol, i.e. 194 mmol, and 1.38 g of potassium carbonate, i.e. 10 mmol, i.e. 5.2 mol % with respect to the p-cresol, and 50 g of methylanisole, i.e. 409 mmol, are introduced into the reactor. The mixture is heated to 160° C. This temperature is maintained throughout the synthesis.

9.9 g of dimethyl carbonate, i.e. 110 mmol, are introduced. The reactor is then fed with continuous flows of 72 mmol/h of dimethyl carbonate and of 60 mmol/h of p-cresol. After reacting for 32 hours, the introduction is continued of only dimethyl carbonate with the same flow rate for 10 hours. The methanol is distilled off as it is formed.

303 g of 4-methylanisole, i.e. 2 480 mmol, are obtained, which corresponds to a yield of 98%.

The mean rate of formation of the 4-methylanisole for the amount of catalyst used is 4.9 mol/mol.h.

EXAMPLE 3

Synthesis of 4-chloroanisole

The assembly used is the same as that in Example 1.

64.3 g of 4-chlorophenol, i.e. 500 mmol, and 2.8 g of potassium carbonate, i.e. 20 mmol, i.e. 4 mol % with respect to the 4-chlorophenol, are introduced into the reactor.

The mixture is heated to 160° C. and this temperature is maintained throughout the synthesis.

19.7 g of dimethyl carbonate, i.e. 219 mmol, are then introduced. The reactor is subsequently fed continuously with dimethyl carbonate until the 4-chlorophenol has been completely consumed. Thus, for 4.5 hours, the reactor is fed with a continuous flow of 150 mmol/h of dimethyl carbonate.

The methanol in the reaction mixture is distilled off as it is formed.

70.6 g of 4-chloroanisole, i.e. 495 mmol, are obtained, which corresponds to a yield of 99%.

The mean rate of formation of the 4-chloroanisole for the amount of catalyst used is 5.5 mol/mol.h.

EXAMPLE 4

Synthesis of 2-methoxynaphthalene

The assembly used is the same as that in Example 1.

72.1 g of 2-naphthol, i.e. 500 mmol, and 5.5 g of potassium carbonate, i.e. 40 mmol, i.e. 8 mol % with respect to the 2-naphthol, are introduced into the reactor. The mixture is heated to 160° C. and this temperature is maintained throughout the synthesis.

18.7 g of dimethyl carbonate, i.e. 207 mmol, are then introduced. The reactor is subsequently fed continuously with dimethyl carbonate until the 2-naphthol has been completely consumed. Thus, for 6 hours, the reactor is fed with a continuous flow of 150 mmol/h of dimethyl carbonate.

The methanol produced is distilled off as it is formed.

75.9 g of 2-methoxynaphthalene, i.e. 480 mmol, are obtained, which corresponds to a yield of 96%.

The mean rate of formation of the 2-methoxynaphthalene for the amount of catalyst used is 2 mol/mol.h.

EXAMPLE 5

Synthesis of 4-ethoxytoluene

The assembly used is the same as that in Example 1.

54 g of p-cresol, i.e. 500 mmol, and 2.8 g of potassium carbonate, i.e. 20 mmol, i.e. 4 mol % with respect to the p-cresol, are introduced into the reactor. The mixture is heated to 160° C. and this temperature is maintained throughout the synthesis.

25.1 g of diethyl carbonate, i.e. 212 mmol, are then introduced. The reactor is subsequently fed with diethyl carbonate with a continuous flow of 50 mmol/h for 12 hours.

The ethanol produced is distilled off as it is formed.

63.8 g of 4-ethoxytoluene, i.e. 469 mmol, are obtained, which corresponds to a yield of 94%.

The mean rate of formation of the 4-ethoxytoluene for the amount of catalyst used is 2 mol/mol.h.

EXAMPLE 6

Synthesis of Anisole

The assembly used is the same as that in Example 1.

47 g of phenol, i.e. 500 mmol, and 2.8 g of potassium carbonate, i.e. 20 mmol, i.e. 4 mol % with respect to the phenol, are introduced into the reactor. The mixture is heated to 150–160° C. and this temperature is maintained throughout the synthesis.

9.9 g of dimethyl carbonate, i.e. 110 mmol, are then introduced. The reactor is subsequently fed with dimethyl carbonate with a continuous flow of 80 mmol/h for 8 hours.

The methanol produced is distilled off as it is formed. 41.6 g of anisole, i.e. 385 mmol, are obtained, which corresponds to a yield of 77%.

The mean rate of formation of the anisole for the amount of catalyst used is 2.4 mol/mol.h.

EXAMPLE 7

Synthesis of 2-hydroxy-4-methoxybenzophenone

The assembly used is the same as that in Example 1.

107.1 g of 2,4-dihydroxybenzophenone, i.e. 500 mmol, and 2.8 g of potassium carbonate, i.e. 20 mmol, i.e. 4 mol % with respect to the 2,4-dihydroxybenzophenone, are introduced into the reactor. The mixture is heated to 160° C. and this temperature is maintained throughout the synthesis.

22.4 g of dimethyl carbonate, i.e. 249 mmol, are then introduced. The reactor is subsequently fed with dimethyl carbonate with a continuous flow of 60 mmol/h for 10 hours.

The methanol produced is distilled off as it is formed.

412 mmol of 2-hydroxy-4-methoxybenzophenone are obtained, which corresponds to a yield of 82%. Only traces of the diether are obtained.

The mean rate of formation of the 2-hydroxy-4-methoxybenzophenone for the amount of catalyst used is 2 mol/mol.h.

EXAMPLE 8

Synthesis of Guaiacol

The assembly used is the same as that in Example 1.

55 g of catechol, i.e. 500 mmol, and 5.5 g of potassium carbonate, i.e. 40 mmol, i.e. 8 mol % with respect to the catechol, are introduced into the reactor.

The mixture is heated to 160° C. and this temperature is maintained throughout the synthesis.

18 g of dimethyl carbonate, i.e. 200 mmol, are then introduced. The reactor is subsequently fed with dimethyl carbonate with a continuous flow of 100 mmol/h for 3 hours.

The methanol produced is distilled off as it is formed.

29.8 g of guaiacol, the monomethyl ether compound, i.e. 240 mmol, are obtained, which corresponds to a yield of 48%, and only 6% of dimethyl ether, veratrole, are obtained.

What is claimed is:

1. A process for the synthesis of aryl alkyl monoethers by reaction of a phenol compound which comprises one or more hydroxyl groups attached to the aromatic cyclic system, and of a dialkyl carbonate, wherein said process is carried out without a solvent, at a pressure of between $0.93 \times 10^5$ Pa and $1.07 \times 10^5$ Pa, at a temperature of between 100° C. and 200° C., in the presence of a catalyst consisting of neutral potassium carbonate, wherein the amount of said dialkyl carbonate is between 0.9 and 5 mole per mole of said phenol compound and wherein said dialkyl carbonate is added gradually to the reaction mixture.

2. The process according to claim 1, wherein said phenol compound is a compound of formula

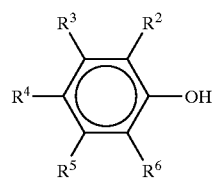

(I)

wherein $R^2$, $R^3$, $R^4$, $R^5$ and $R^6$, are identical or different, and each one represents a hydrogen atom, a substituted or unsubstituted, saturated or unsaturated, $C_1$ to $C_{20}$ alkyl radical, a substituted or unsubstituted, aryl or aryl alkyl group, a halogen atom, a nitrile or nitro group or a group of formula:

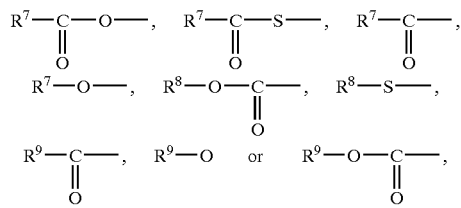

in which $R^7$ is a $C_1$ to $C_{20}$ aliphatic radical, a $C_1$ to $C_{12}$ aralykyl radical or a $C_8$ to $C_{14}$ aromatic radical, $R^8$ is a $C_1$ to $C_{20}$ aliphatic radical, a $C_7$ to $C_{12}$ aralykyl radical or a $C_8$ to $C_{14}$ aromatic radical, and $R^9$ is a hydrogen atom.

3. The process according to claim 2 wherein two adjacent groups $R^2R^3$, $R^3R^4$, $R^4R^5$ or $R^8R^6$ radicals are connected to one another to form a saturated or unsaturated aliphatic ring, an aromatic ring or a saturated or unsaturated heterocycle which are unsubstituted or substituted by groups as for $R^2$ to $R_6$.

4. The process according to claim 1 wherein said dialkyl carbonate is dimethyl carbonate or diethyl carbonate.

5. The process according to claim 1 wherein the amount of catalyst used is between 0.01 and 0.1 mole per mole of said phenol compound.

6. The process according to claim 1 wherein the reaction temperature is between 140° C. and 180° C.

7. The process according to claim 1 wherein said dialkyl carbonate is added continuously to the reaction mixture with a flow rate of between 1 and 20 mole/h per mole of said catalyst.

8. The process according to claim 1 which comprises the following steps: (1) introducing said phenol compound, said catalyst and a portion of said aryl alkyl ether if available into a reactor to form an heterogeneous mixture; (2) heating said mixture to a temperature at 100° C.–200° C., whereby said mixture becomes homogenous; (3) gradually introducing said dialkyl carbonate with a flow rate of 0.5 mole–20 mole per hour per mole or said catalyst; (4) adding gradually the remainder of said dialkyl carbonate and purifying the product said aryl alkyl ether by distillation.

9. The process according to claim 8 wherein a portion of the amount of phenol compound is present initially in the reactor and the ether portion is added gradually to the reaction mixture.

10. The process according to claim 1 which is completed in 3–33 hours.

* * * * *